United States Patent [19]

Vora

[11] Patent Number: 4,467,128
[45] Date of Patent: Aug. 21, 1984

[54] INTEGRATED HF REGENERATION IN AROMATIC HYDROCARBON ALKYLATION PROCESS

[75] Inventor: Bipin V. Vora, Elk Grove Village, Ill.

[73] Assignee: UOP Inc., Des Plaines, Ill.

[21] Appl. No.: 534,912

[22] Filed: Sep. 22, 1983

[51] Int. Cl.³ .............................................. C07C 2/66
[52] U.S. Cl. .................................... 585/456; 585/464
[58] Field of Search .............................. 585/456, 464

[56] References Cited

U.S. PATENT DOCUMENTS

| | | | |
|---|---|---|---|
| 3,494,971 | 2/1970 | Fenske | 260/671 |
| 3,950,448 | 4/1976 | Witt | 260/671 B |
| 4,195,191 | 3/1980 | Boney | 585/706 |
| 4,225,737 | 9/1980 | Mikulicz et al. | 585/464 |
| 4,237,327 | 12/1980 | Winter | 585/464 |
| 4,237,328 | 12/1980 | Winter | 585/464 |
| 4,239,931 | 12/1980 | Mikulicz | 585/723 |

Primary Examiner—Curtis R. Davis
Attorney, Agent, or Firm—James R. Hoatson, Jr.; John F. Spears, Jr.; William H. Page II

[57] ABSTRACT

A process is disclosed for the production of alkylaromatic hydrocarbons by the HF catalyzed reaction of an aromatic hydrocarbon with a $C_8$-plus acyclic olefin. A portion of the HF used as catalyst is regenerated by passage into a stripping column which has a primary function of stripping dissolved HF out of a hydrocarbonaceous mixture produced in the alkylation zone. This eliminates the requirement for a separate HF regeneration column and the costs associated with this column.

11 Claims, 1 Drawing Figure

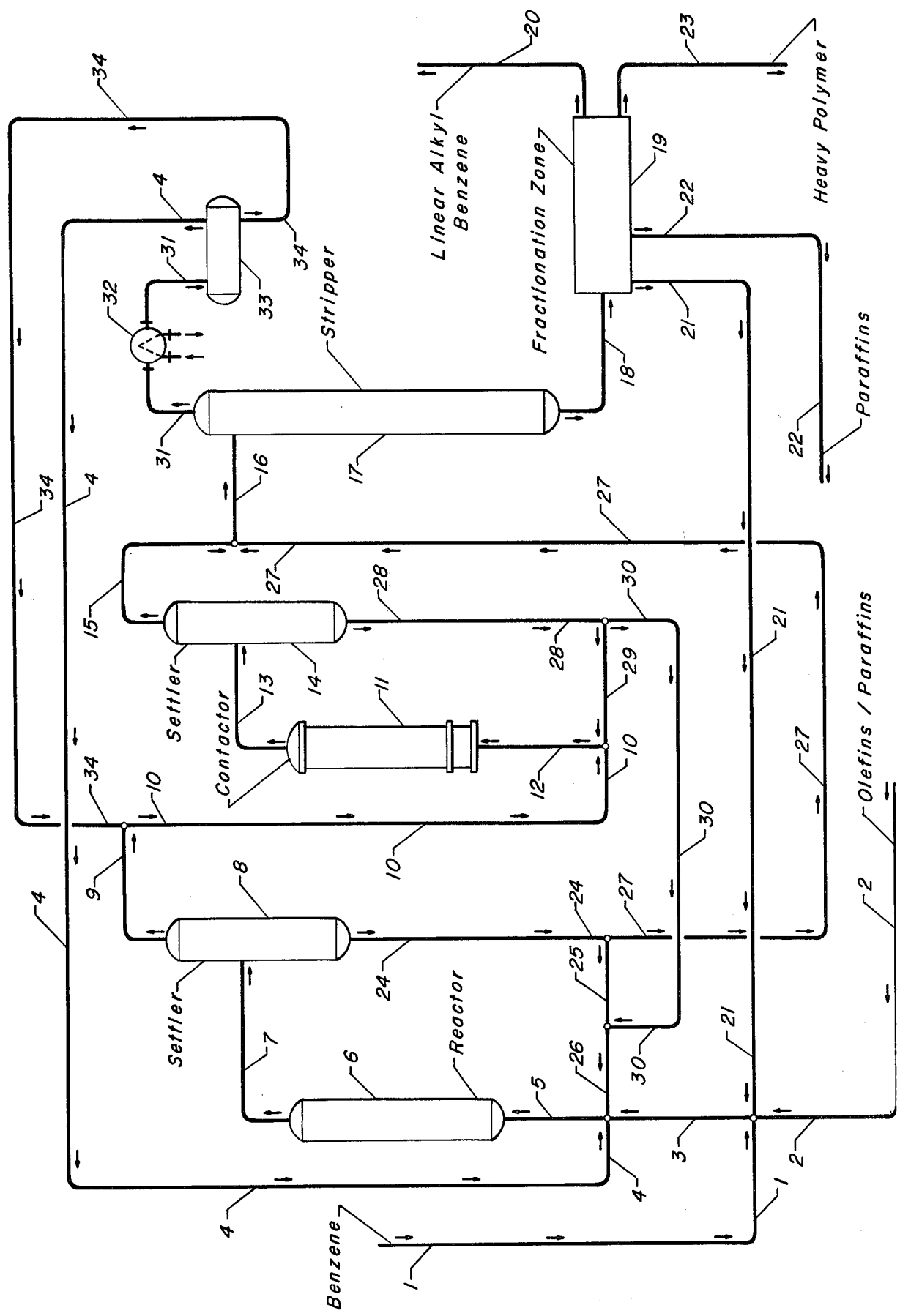

INTEGRATED HF REGENERATION IN AROMATIC HYDROCARBON ALKYLATION PROCESS

FIELD OF THE INVENTION

The invention relates to an aromatic hydrocarbon alkylation process. The invention directly relates to a process for the production of alkylaromatic hydrocarbons by the HF catalyzed reaction of an alkylatable aromatic hydrocarbon with an acyclic olefinic hydrocarbon. An example of this is the HF catalyzed alkylation of benzene with a $C_8$-plus normal olefinic hydrocarbon to create a linear alkylbenzene which is highly suitable for the production of detergents. The invention specifically relates to the method utilized to regenerate the HF by removing high boiling hydrocarbonaceous compounds which tend to accumulate in the liquid phase HF.

PRIOR ART

The alkylation of benzene with acyclic olefins is a widely practiced commercial process. This process is performed to produce a variety of chemical compounds which may be end products or may be used as intermediates in the production of other valuable industrial chemicals. One of the most significant processes for the alkylation of aromatic hydrocarbons employs liquid phase HF as the catalyst and is performed to produce linear alkylbenzenes which are then converted into detergents by sulfonation and neutralization. The preferred arrangement of the alkylation zone, suitable reaction conditions, feed materials and an overall description of an alkylation process of the preferred type is presented in U.S. Pat. No. 3,494,971 issued to E. R. Fenske. This reference is also relevant for its showing of the traditional method of regenerating the liquid phase HF employed as a catalyst in such a "detergent alkylation" process. This regeneration method comprises passing a small stream of HF removed from the initial reaction stage into a stripping column. The HF is removed overhead as a vapor and then condensed leaving a high boiling mass referred to as "tar" which is withdrawn from the stripping column as a net bottoms stream. U.S. Pat. Nos. 3,950,448 issued to P. A. Witt and 4,237,327 issued to G. R. Winter are pertinent for their teaching in regard to the operation and integration of HF regeneration columns into a detergent alkylation process and the possible arrangements of the fractionation zones of detergent alkylation processes. This includes the use of an HF stripping column which receives the entire hydrocarbonaceous effluent stream of the alkylation zone proper.

The regeneration of liquid phase HF which is used as a catalyst in the production of motor fuels by the alkylation of isobutane with a normal butylene is also known in the art. This regeneration is performed to remove heavy polymeric substances which are more soluble in the liquid phase HF than in the hydrocarbon mixture present in the reaction zone. This regeneration was traditionally done by passing a small stream of HF into a stripping column and separating the heavy polymers into a small bottoms stream. U.S. Pat. Nos. 4,195,191 issued to W. G. Boney and 4,239,931 issued to M. Z. Mikulicz illustrate a different approach to solving the problem of the gradual accumulation of these heavy materials in the HF. In these references, the hydrocarbonaceous effluent of the alkylation zone is heated to increase the solubility of HF therein and the heated hydrocarbon stream is then admixed with a small stream of the used HF. This admixture of HF and hydrocarbons is then passed into a stripping column and separated into at least an overhead containing polymer-free HF, a sidecut stream and a bottoms stream containing the product alkylate and the polymers.

BRIEF SUMMARY OF THE INVENTION

The invention provides an improved process for alkylating aromatic hydrocarbons which eliminates the need for an HF regeneration column. The HF is regenerated by continuously passing a small stream of the used HF into the top portion of a stripping column which removes dissolved HF from the hydrocarbonaceous effluent stream of the alkylation zone. The stripping column is operated in a manner which prevents the presence of HF in the stripping column bottoms stream. To this end the HF and a portion of the lightest hydrocarbon present in the hydrocarbonaceous effluent are removed overhead. Both the high boiling compounds present in the HF and the high boiling compounds present in the hydrocarbonaceous effluent become concentrated into the stripping column bottoms stream.

One embodiment of the invention may be characterized as a process for the production of linear alkylaromatic hydrocarbons which comprises the steps of reacting a feed aromatic hydrocarbon with a $C_8$-plus normal olefinic hydrocarbon in the presence of liquid phase HF having a first purity, and which acts as an alkylation catalyst, in a reaction zone and thereby producing a first hydrocarbon admixture comprising residual feed aromatic hydrocarbon and a product linear alkylaromatic hydrocarbon; contacting said hydrocarbon admixture with liquid phase HF having a higher second purity in a contacting zone and thereby producing a second hydrocarbon admixture comprising the feed aromatic hydrocarbon and the product linear alkylaromatic hydrocarbon; passing the second hydrocarbon admixture into a fractionation column; passing an HF stream comprising HF withdrawn from the reaction zone, and which contains dissolved high boiling hydrocarbons, into the fractionation column; separating the compounds entering the fractionation column into an overhead vapor stream comprising HF and a net bottoms comprising the product alkylaromatic hydrocarbon and high boiling hydrocarbons; recovering the product alkylaromatic hydrocarbon from the net bottoms stream; and recovering high purity liquid HF from the overhead vapor stream and passing recovered high purity HF into the contacting zone.

BRIEF DESCRIPTION OF DRAWING

The drawing is a simplified process flow diagram of a preferred embodiment of the subject invention. The drawing has been simplified by the deletion of various types of process apparatus such as vessel internals, control systems, reboilers, etc., which are normally employed in a process of this type. This presentation of one preferred embodiment of the invention is not intended to preclude from the scope of the invention those other embodiments set out herein or which are the result of the normal and reasonable modification of those embodiments.

Referring now to the drawing, a first feed stream comprising high purity benzene is passed into the process through line 1 and is admixed with a stream comprising an admixture of $C_{10}$ to $C_{15}$ normal olefins and normal paraffins carried by line 2. The two feed streams are also admixed with a recycle stream comprising benzene carried by line 21 with this mixture of benzene, olefins and paraffins being transported through line 3. A second recycle stream which comprises benzene and which is carried by line 4 is then admixed into the hydrocarbons of line 3 together with a stream of liquid phase HF carried by line 26. The resultant admixture of benzene, olefins, paraffins and HF is passed into the lower portion of the alkylation reactor 6 through line 5. This contacting of the olefinic feed hydrocarbon with the benzene in the presence of the catalytically effective HF results predominantly in an alkylation reaction occurring between the benzene and the olefinic hydrocarbon within the reactor 6.

The contents of the reactor are maintained in a state of agitation through the use of mixing means within the reactor, with an effluent stream comprising an admixture of the residual entering hydrocarbons, the product alkylbenzene and liquid phase HF being removed from the reactor in line 7. This liquid phase stream is separated in a first settler 8 into a lower liquid phase of HF which is withdrawn through line 24 and an upper phase of the less dense hydrocarbons which is withdrawn as a hydrocarbon stream carried by line 9. The hydrocarbon stream carried by line 9 is admixed with a stream of liquid phase HF transported through line 34 and is then directed through line 10 to the junction with line 29 at which it is admixed with a second stream of liquid phase HF. This mixture of benzene, normal paraffins, the product alkylbenzene and liquid phase HF is passed into a contactor 11 through line 12 and is therein subjected to conditions which result in the production of a detergent alkylate of increased quality. The effluent stream of the contactor, which has about the same composition as the material charged to the contactor, is withdrawn through line 13 and passed into a second settler 14. The effluent stream of the contactor 11 separates due to the quiescent conditions maintained within the settler into a denser HF phase which is withdrawn through line 28 and a less dense hydrocarbon phase which is withdrawn through line 15. The hydrocarbonaceous mixture flowing through line 15 is referred to herein as the effluent of the alkylation zone.

The liquid phase HF employed within the contactor 11 is of a higher purity than the HF employed as a catalyst within the reactor 6. To counteract the gradual dilution of the HF by accumulated hydrocarbonaceous side products of the alkylation reaction, a small portion of the HF circulating through the reactor loop is withdrawn through line 27 for regeneration. This HF which is to be regenerated is withdrawn from the HF removed from the first settler 8, with the remainder of the HF from the settler 8 being carried by line 25 and passed into the reactor 6. The HF withdrawn from the second settler 14 is divided into a first portion which is returned to the contactor through line 29 and a second portion which is charged to the reactor HF loop through line 30 at a rate necessary to replace the HF withdrawn for regeneration. The stream of the HF which is to be regenerated is passed into a fractionation column 17, referred to herein as a stripping column or stripper, through lines 27 and 16.

The HF flowing through line 27 is preferably admixed with the effluent stream of the alkylation zone carried by line 15 and passed into the top of column 17. The fractionation column is designed and operated to eject all of the entering HF and a significant percentage of the entering benzene as an overhead vapor stream removed through line 31. The overhead vapor stream is condensed in the overhead condenser 32 and passed into the overhead receiver 33 wherein it is separated into a liquid HF phase and a less dense liquid hydrocarbon phase. These two phases are separately withdrawn and recirculated through lines 4 and 34. The remainder of the hydrocarbons which enter the stripper 17 are concentrated into a net bottom stream removed through line 18. This stream comprises unreacted benzene, normal paraffins from the feed stream of line 2, the product linear alkylbenzene and a very small amount of high boiling side-products. These hydrocarbons are separated in the fractionation zone 19 into a benzene recycle stream carried by line 21, a high purity stream of paraffins removed through line 22, a product stream of linear alkylbenzene removed through line 20 and a small stream referred to as heavy polymer or heavy alkylate removed in line 23. The material carried by line 23 comprises the hydrocarbons withdrawn from the prior art fractionation zones as heavy alkylate which was present in the net stripper bottoms stream plus the heavy hydrocarbons which were previously withdrawn from the HF regeneration column of prior art processes.

DETAILED DESCRIPTION

One of the more important commercially performed alkylation reactions is the production of detergent grade alkylated aromatic hydrocarbons. This material, often referred to as "detergent alkylate", is normally formed by the reaction of benzene with an olefinic hydrocarbon having from seven to twenty carbon atoms per molecule. A better quality detergent precursor normally results from the use of olefinic hydrocarbons having from about ten to fifteen carbon atoms per molecule. The detergents produced from the resulting alkylated aromatic hydrocarbons are classified either as "soft" if they meet certain standards of biodegradability or as "hard" if they are relatively nonbiodegradable. Soft detergents result from using a long-chain or normal monoolefin as the olefinic reactant. The preferred method of producing these linear olefins is by the dehydrogenation of the corresponding normal paraffins. The dehydrogenation zone may be integrated with the detergent alkylation process as described in U.S. Pat. Nos. 3,413,373; 3,484,498 and 3,494,971. Hard detergents result from the use of branched chain olefins such as propylene tetramer produced in a catalytic condensation process. The use of soft detergents is becoming more widespread, and the subject invention will therefore be discussed primarily in terms of detergent alkylate intended for the production of soft detergents.

The subject process utilizes hydrogen fluoride (HF) as the catalyst. HF is a very effective alkylation catalyst and one which, through proper selection of reaction conditions, can be made very selective to the desired monoalkylation reaction. Nevertheless, a number of side reactions do occur. These side reactions include the oligomerization of two or three of the acyclic feed olefinic hydrocarbons, the dialkylation of the feed aromatic hydrocarbon and the reaction of two or more of the feed aromatic hydrocarbons with a single molecule of the feed olefinic hydrocarbons. This results in a very large number of different hydrocarbons being produced as side products, especially when feed olefins having a range of carbon numbers is utilized as one of the feedstocks. Most of these side product hydrocarbons have rather low volatilities compared to the desired linear alkylbenzenes. Some of the side products are soluble in the bulk hydrocarbon streams of the subject process and are removed from the process as a small stream of "heavy alkylate" withdrawn from the terminal fractionation column of the product recovery zone. This is shown for example in the previously cited U.S. Pat. No. 3,950,448. Other side product hydrocarbons are preferentially soluble in the liquid phase HF. These HF soluble hydrocarbons eventually accumulate in the HF to a concentration which is undesirably high. The accumulated hydrocarbons begin to reduce the purity of the HF below that which optimizes the performance of the alkylation process. It has therefore become a standard practice to provide an HF regeneration system for the alkylation process, with this system typically comprising a stripping column in which the more volatile HF is separated from higher boiling side product hydrocarbons dissolved in the HF.

It is an objective of the subject invention to provide an improved process for the production of detergent alkylate by eliminating the need for an HF regeneration system. It is another objective of the subject invention to reduce the inventory volume of HF required in an aromatic hydrocarbon alkylation process. Another objective of the subject process is to reduce the capital and utilities cost of a process for the production of linear alkylbenzenes.

In the subject process the prior art HF regeneration column is eliminated by continuously passing a small stream of used HF into a fractionation column which is used to strip dissolved HF out of the hydrocarbons discharged from the alkylation zone. Preferably, this stream is first admixed with the hydrocarbon admixture charged to the top portion of this column. Operation of the stripping column in this manner results in excellent concentration of both the hydrocarbon soluble reaction by-products and the HF soluble by-products into the bottoms stream of the fractionation column. The flow rate of the used HF is low in comparison to the flow rate of the hydrocarbon admixture which enters the column from the alkylation zone. For example, the HF being regenerated may be about 5 wt.% of the total hydrocarbons fed to the fractionation column from the alkylation zone. Although all or a portion of the HF could be passed into the fractionation column at a point below the main feed, this practice is not preferred. It is preferred that the HF is admixed with the hydrocarbons after the hydrocarbons have been heated. This may be done by the customary HF stripper feed heater. The heating of the HF preferably allows all of the HF undergoing regeneration to become dissolved in the hydrocarbon phase entering the stripping column.

The aromatic hydrocarbon which is alkylated in the subject process is preferably benzene, but may be a higher molecular weight aromatic hydrocarbon. The feed aromatic hydrocarbon may therefore be toluene, a xylene, ethylbenzene, phenol, naphthalene, etc. The feed olefinic hydrocarbon which is consumed in the production of the detergent alkylate may have from about seven to twenty carbon atoms per molecule. The olefinic hydrocarbon may be propylene tetramer. The preferred olefinic hydrocarbons are aliphatic monoolefins having from ten to fifteen carbon atoms per molecule. When the olefinic hydrocarbons are produced in a dehydrogenation process which is integrated with the alkylation process, it is a common practice to pass an unseparated paraffin/olefin mixture produced as the effluent of dehydrogenation process into the alkylation process as the olefin-containing feed stream. This is basically because of the high cost of separating olefins and paraffins of the same carbon number, but the presence of the paraffins is also beneficial. Normal paraffins act as a heat sink for the heat of reaction and promote monoalkylation by decreasing the overall olefin concentration. The olefin-containing feed stream charged to the alkylation process may contain from about 0 to about 90 mole percent straight chain paraffins having the same number of carbon atoms per molecule as the olefinic hydrocarbons. These relatively non-reactive paraffins pass through the alkylation process in the various hydrocarbon phase streams and are eventually separated from the alkylate by fractionation and then recycled to the dehydrogenation process.

Chemical reactions which involve olefinic hydrocarbons and are catalyzed by hydrogen fluoride usually proceed at a very fast rate. To reduce the amount of olefin polymerization and to promote the production of a monoalkylated aromatic product, the reactants are normally subjected to vigorous mixing and agitation at the point of initial contact of the olefinic hydrocarbons and the liquid-phase hydrogen fluoride. The desired result is a uniform dispersion and intimate contacting of the hydrocarbon and hydrogen fluoride phases and the avoidance of localized high temperatures or localized high concentrations of either the olefinic hydrocarbon or the hydrogen fluoride. The initial contacting of the reactants and the catalyst has been done in a number of different ways. For instance, the olefinic hydrocarbons have been sprayed into a mixture of hydrogen fluoride and hydrocarbons through nozzles, and mixtures of the reactants have been released into eductors as high velocity streams which cause the eduction and admixture of the hydrogen fluoride. U.S. Pat. No. 4,134,734 describes a unitary reactor for the production of detergent alkylate. U.S. Pat. No. 4,072,730 describes a process for producing detergent alkylate in which a centrifugal pump is utilized as the first reaction zone due to the intense agitation which occurs within the pump.

The alkylation zone preferably has an overall arrangement similar to that shown in previously referred to U.S. Pat. No. 3,494,971. In this arrangement the two feed hydrocarbons and liquid phase HF are charged to a reactor. The effluent of this reactor is passed into a first settling zone and separated into HF and hydrocarbon phases. The HF is withdrawn and divided into a portion passed into the HF stripping column for regeneration and a portion returned to the reactor. The hydrocarbon phase is withdrawn from the first settling zone and charged to a contactor, which is sometimes referred to as a second "reactor", as the only hydrocarbon charged to the contactor. The HF charged to the contactor is a mixture of newly regenerated HF and HF withdrawn from a second settling zone, which receives the total effluent of the contactor. A portion of the HF withdrawn from the second settling zone is charged to the reactor to replace the HF withdrawn for regeneration. The hydrocarbon phase which is withdrawn from the second settling zone is the alkylation zone effluent stream. This stream is passed into a stripping column in which dissolved HF is removed overhead along with some of the feed aromatic hydrocarbon. The net bottoms of this HF stripping column is charged to the fractionation zone of the subject process.

The reaction zone and the contacting zone are maintained at alkylation-promoting conditions. As used herein, the term "alkylation-promoting conditions" is intended to include a pressure sufficient to maintain the reactants and HF in a liquid phase. A general range of operating pressures is from about 2 to 41 atmospheres absolute. The temperature range covered by this set of conditions is from about −20° to about 95° C., but the reaction is preferably conducted at a temperature of from 20° to 70° C. The volumetric ratio of HF to the total amount of hydrocarbons entering the reactor should be maintained within the broad range of from about 0.2:1.0 to about 10:1. A preferred range for this ratio is from 0.5:1 to 2:1. To lessen the production of polyalkylated benzenes and to reduce the amount of olefin polymerization in the reactor, the mole ratio of benzene of the monoolefin at the point of initial olefin-acid contact is maintained above 1:1, but preferably below 14:1. A range of typical commercial ratios is from 3:1 to about 10:1.

The conditions maintained within the contactor are similar to the conditions maintained in the reactor, but some adjustment is required. For instance, since essentially all of the olefin is preferably consumed in the reactor, the hydrocarbon stream fed to the contactor is substantially free of olefins. There is therefore no benzene to olefin ratio to be specified. The same pressure range may be used in the contactor as in the reactor, but a higher temperature is preferred. This higher temperature should be at least 6 to 10 Centigrade degrees above that used in the reaction zone. All temperatures specified herein are intended to refer to the average temperature of the liquid stream entering the respective zone.

The HF-hydrocarbon ratio maintained in the contacting zone will normally be slightly lower, and a typical ratio is about 1:1. The purity of acid used in the contactor will, however, be higher. This is preferred because of the greater effectiveness of higher purity acid for the treatment of the alkylate. This treatment consists of the defluorination of the alkylate product and the extraction of naphthalenes and anthracenes. A higher acid purity is obtained by admixing the newly regenerated acid into the alkylate-containing hydrocarbon stream entering the contacting zone (contactor). The recycle acid for use in the reaction zone (reactor) is withdrawn from the second settling zone and therefore contains a higher concentration of high molecular weight hydrocarbonaceous impurities. The acid used in the reactor preferably contains about 85–92 wt.% HF and will typically be about 90 wt.% HF. The acid used in the contactor preferably contains more than 90 wt.% HF and is typically about 93–94 wt.% HF.

The effluent streams leaving the reactor and the contactor will typically be an intimate admixture of liquid phase hydrocarbons and liquid phase hydrogen fluoride. They may be in the form of a true emulsion. A considerable residence time is normally required to separate these two liquid phases, and the effluent streams are therefore passed into quiescent settling zones. The two settling zones will normally be maintained at a temperature which is set by the entering HF-hydrocarbon mixtures withdrawn from the respective upstream zones. They will therefore be at substantially the same temperature as the immediately upstream reaction or contacting zone. The same is also normally true for the pressures used in the settling zones after adjustment for any pressure change due to liquid flow and elevation differences. The settling zones may however be downstream of control valves and therefore operated at a somewhat reduced pressure. This reduced pressure, however, must be superatmospheric and sufficient to maintain liquid phase conditions. A residence time for both the acid and hydrocarbon phases in the settling zones should be in excess of 90 seconds but less than 30 minutes.

As previously stated, the hydrocarbonaceous phase removed from the second settling zone is preferably passed into a fractionation column commonly referred to as the HF stripping column. This column derives its name from its basic function in the prior art of preventing the passage of HF into the downstream fractionation zone. Representative conditions for the operation of the HF stripping column include an overhead vapor temperature of about 250° F. at a pressure of approximately 36 psig. There is normally no external reflux to this column. The overhead vapor stream of the HF stripping column is normally completely condensed by cooling it to about 100° F. or less and is then decanted and recirculated as described above. The entire hydrocarbonaceous effluent of the second settling zone is normally passed onto the top tray of this column. As previously set out, in the subject invention the stream of HF which is to be regenerated is also passed into the upper portion of the HF stripping column. This may be done in several ways but preferably comprises passing at least a portion of the regeneration HF stream into the column in admixture with the main hydrocarbon feed stream at the top of the column. All of the HF is preferably dissolved in the hydrocarbons of this admixture. This is believed desirable to minimize corrosion problems. The solubility of the HF may be enhanced by first heating the hydrocarbons above the temperature maintained in the contacting zone.

One embodiment of the invention may accordingly be characterized as a process for the production of alkylaromatic hydrocarbons which comprises the steps of contacting a feed aromatic hydrocarbon with an acyclic feed olefinic hydrocarbon which has more than eight carbon atoms per molecule with liquid phase HF in a reaction zone maintained at alkylation-promoting conditions and thereby forming a reaction zone effluent stream which comprises the feed aromatic hydrocarbon, HF, a product alkylaromatic hydrocarbon and a small amount of high boiling reaction by-products; separating substantially all of the hydrocarbons present in the reaction zone effluent stream from the liquid phase HF present in the reaction zone effluent stream, and thereby forming a first hydrocarbon stream and a first HF stream, passing the thus derived first hydrocarbon stream into a contacting zone wherein the said first hydrocarbon stream is contacted with liquid phase HF having a higher purity than the HF which is employed in the reaction zone and thereby forming a contacting zone effluent stream which comprises the feed aromatic hydrocarbon, HF, the product alkylaromatic hydrocarbon and the various high boiling hydrocarbons present in the process; separating substantially all of the hydrocarbons present in the contacting zone effluent stream from the liquid phase HF present in the contacting zone effluent stream and thereby forming a second hydrocarbon process stream and a second HF stream; passing a first portion of the second HF stream into the contacting zone and a second portion of the second HF stream into the reaction zone; passing a first portion of the first HF stream into the reaction zone; passing a second portion of the first HF stream into a fractionation column operated at fractionation-promoting conditions in admixture with the second hydrocarbon process stream; condensing the overhead vapor stream of the fractionation column and thereby forming liquid HF and liquid hydrocarbons which are separated into a third HF stream and a third hydrocarbon stream, which comprises the feed aromatic hydrocarbon; passing the third HF stream into the contacting zone; and recovering the product alkylaromatic hydrocarbon from a net bottoms stream removed from the fractionation column.

The previously cited patents also describe fractionation systems and conditions suitable for use as an effective separation zone to recover the product alkylate from the bottoms stream of the HF stripping column. For instance, the bottoms stream of the HF stripping column is preferably passed into a second fractionation column referred to as a benzene column. The benzene column is operated under conditions effective to cause the division of the entering hydrocarbons into a high purity benzene stream which is removed as the overhead liquid and a bottoms stream containing the alkylate product. This bottoms stream is passed into a third fractionation column referred to as a paraffin column. The non-reactive paraffins are removed as an overhead liquid stream. The bottoms stream of the third fractionation column comprises the product alkylate and the higher molecular weight side product hydrocarbons formed in the reaction zone. This bottoms stream is passed into a fourth fractionation column which produces a high purity overhead stream containing the detergent alkylate. A bottoms stream comprising such high boiling by-products as polymerized olefins and polyalkylated benzenes (heavy alkylate) is removed from the fourth column for disposal. The third and the fourth fractionation columns are normally operated at a subatmospheric pressure. An alternative method of performing this separation is disclosed in previously cited U.S. Pat. No. 3,950,448. In this arrangement the bottoms steam of the HF stripping column is passed into a column referred to as a paraffin column. All of the feed aromatic hydrocarbon is withdrawn from the HF stripping column in an overhead stream or as a liquid stream removed below a contact condenser located in the top of the column. The net bottoms stream of the HF stripping column is therefore devoid of the feed aromatic hydrocarbon. This bottoms stream is then separated in the same manner as set out above.

The product linear alkylbenzene obtained in this manner may be used as the raw material or feedstock for the preparation of a true detergent or surface active agent. Excellent detergents may be produced from the alkylbenzene by first performing a sulfonation to produce a sulfonic acid derivative by contact with an agent such as sulfur trioxide. This derivative is then neutralized by passage into a saponification zone. The neutralization comprises the admixture of the sulfonation reactor effluent with an aqueous stream containing ammonia, sodium hydroxide or potassium hydroxide. The alkaline compound neutralizes the sulfonic acid to produce sulfonates such as water-soluble sodium alkylaromatic monosulfonate salts. Further information on sulfonation and saponification are available from many standard references and from U.S. Pat. Nos. 4,036,875 and 4,240,978. The product alkylate can also be subjected to other chemical reactions to produce other types of detergents. For instance, the alkylate may be nitrated to form a substituted mono-nitro derivative which is then catalytically reduced to a mono-amino-substituted analog such as an alkylaniline or alkyltoluidine. The amine is then condensed with ethylene oxide or propylene oxide to introduce a hydrophilic polyoxyalkylene group on the amino nitrogen atom. This preferably forms a polyoxyalkylated detergent product having from about 10 to 30 oxyalkylene units per molecule. The condensation may be catalyzed by the presence of an alkaline catalyst such as sodium hydroxide.

The normal paraffin stream which is preferably produced in the fractionation zone is preferably passed into a catalytic paraffin dehydrogenation zone. In this zone the paraffins in admixture with hydrogen are contacted with a catalyst at an elevated temperature to produce additional feed olefinic hydrocarbons. A preferred set of dehydrogenation conditions includes a temperature of about 420° to about 545° C., a pressure from about 0.7 to about 13 atmospheres (preferably about 2.0) and a liquid hourly space velocity in the range of about 10 to 36. A catalyst comprising platinum and tin supported on alumina spheres is preferred although other catalysts can be substituted. The recycled paraffins together with any feed paraffins charged to the overall process are heated to reaction conditions and preferably passed through a single catalyst bed. The effluent of the catalyst bed is partially condensed to allow a simple separation of a hydrogen-rich gas, a portion of which is withdrawn with the remainder being recycled to the reactor. The net condensate is passed into a stripping column wherein all hydrocarbons having fewer carbon atoms per molecule than the desired feed normal olefin(s) are removed overhead as a light ends stream. Further details on suitable dehydrogenation methods may be obtained by reference to U.S. Pat. Nos. 3,391,218; 3,448,165; 3,745,112 and 3,907,921. The catalyst and the configuration of the dehydrogenation reaction zone may be chosen as desired from any commerically feasible type of catalyst and reactor.

I claim as my invention:

1. In a process for the production of alkylaromatic hydrocarbons in which a feed aromatic hydrocarbon is brought into contact with an acyclic $C_8$-plus olefinic hydrocarbon and liquid-phase HF in an alkylation zone at alkylation-promoting conditions to thereby effect the production of the product alkylaromatic hydrocarbon, with a portion of the HF being regenerated by the removal of high boiling hydrocarbonaceous compounds; the improvement which comprises regenerating the HF by passing a stream of the HF into a stripping column in which the hydrocarbonaceous effluent of the alkylation zone is initially fractionated, and recycling high purity regenerated HF recovered from the overhead system of the stripping column to the alkylation zone.

2. A process for the production of linear alkylaromatic hydrocarbons which comprises the steps of:
   (a) reacting a feed aromatic hydrocarbon with a $C_8$-plus normal olefinic hydrocarbon in the presence of liquid phase HF having a first purity, and which acts as an alkylation catalyst, in a reaction zone and thereby producing a first hydrocarbon admixture comprising residual feed aromatic hydrocarbon and a product linear alkylaromatic hydrocarbon;
   (b) contacting said hydrocarbon admixture with liquid phase HF having a higher second purity in a contacting zone and thereby producing a second hydrocarbon admixture comprising the feed aromatic hydrocarbon and the product linear alkylaromatic hydrocarbon;

(c) passing the second hydrocarbon admixture into a fractionation column;

(d) passing an HF stream comprising HF withdrawn from the reaction zone, and which also comprises dissolved high boiling hydrocarbons, into the fractionation column;

(e) separating the compounds entering the fractionation column into an overhead vapor stream comprising HF and a net bottoms stream comprising the product alkylaromatic hydrocarbon;

(f) recovering the product alkylaromatic hydrocarbon from the net bottoms stream; and, (g) recovering high purity liquid HF from the overhead vapor stream, and passing recovered high purity HF into the contacting zone.

3. The process of claim 2 further characterized in that the feed aromatic hydrocarbon is benzene.

4. The process of claim 3 further characterized in that the $C_8$-plus olefinic hydrocarbon is charged to the reaction zone in admixture with a normal paraffinic hydrocarbon having the same number of carbon atoms per molecule.

5. The process of claim 2 further characterized in that the HF stream is passed into the fractionation column in admixture with the second hydrocarbon admixture.

6. A process for the production of alkylaromatic hydrocarbons which comprises the steps of:

(a) contacting a feed aromatic hydrocarbon with an acyclic feed olefinic hydrocarbon which has more than eight carbon atoms per molecule and with liquid phase HF in a reaction zone maintained at alkylation-promoting conditions and thereby forming a reaction zone effluent stream which comprises the feed aromatic hydrocarbon, HF, a product alkylaromatic hydrocarbon and a small amount of high boiling reaction by-products;

(b) separating substantially all of the hydrocarbons present in the reaction zone effluent stream from the liquid phase HF present in the reaction zone effluent stream, and thereby forming a first hydrocarbon stream and a first HF stream, passing the thus derived first hydrocarbon stream into a contacting zone wherein the said first hydrocarbon stream is contacted with liquid phase HF having a higher purity than the HF which is employed in the reaction zone and thereby forming a contacting zone effluent stream which comprises the feed aromatic hydrocarbon, HF and the product alkylaromatic hydrocarbon;

(c) separating substantially all of the hydrocarbons present in the contacting zone effluent stream from the liquid phase HF present in the contacting zone effluent stream and thereby forming a second hydrocarbon process stream and a second HF stream;

(d) passing a first portion of the second HF stream into the contacting zone and a second portion of the second HF stream into the reaction zone;

(e) passing a first portion of the first HF stream into the reaction zone and a second portion of the first HF stream into a fractionation column operated at fractionation-promoting conditions;

(f) passing the second hydrocarbon process stream into the fractionation column;

(g) condensing the overhead vapor stream of the fractionation column and thereby forming liquid HF and liquid hydrocarbons which are separated into a third HF stream and a third hydrocarbon stream, which comprises the feed aromatic hydrocarbon;

(h) passing the third HF stream into the contacting zone; and, (i) recovering the product alkylaromatic hydrocarbon from a net bottoms stream removed from the fractionation column.

7. The process of claim 6 further characterized in that the third hydrocarbon stream is passed into the reaction zone.

8. The process of claim 7 further characterized in that the feed aromatic hydrocarbon is benzene.

9. The process of claim 8 further characterized in that the acyclic feed olefinic hydrocarbon is a $C_{10}$ to $C_{15}$ normal olefin.

10. The process of claim 9 further characterized in that the acyclic feed olefinic hydrocarbon is contained in a mixture of normal olefinic hydrocarbons and normal paraffinic hydrocarbons.

11. The process of claim 9 further characterized in that the second hydrocarbon process stream and the second portion of the first HF stream are passed into the fractination column as an admixture in which the HF is dissolved in the hydrocarbons present in the admixture.

* * * * *